United States Patent
Behler et al.

(10) Patent No.: US 7,384,904 B2
(45) Date of Patent: Jun. 10, 2008

(54) METHOD FOR PRODUCING ALKYL OLIGOGLUCOSIDE AND ALKENYL OLIGOGLUCOSIDE CARBOXYLIC ACID SALTS WITH REDUCED ORGANOCHLORIDE COMPOUNDS

(75) Inventors: Ansgar Behler, Bottrop (DE); Almud Folge, Leichlingen (DE)

(73) Assignee: Cognis Deutschland GmbH & Co. KG, Duesseldorf (DE)

(*) Notice: Subject to any disclaimer, the term of this patent is extended or adjusted under 35 U.S.C. 154(b) by 0 days.

(21) Appl. No.: 10/539,668

(22) PCT Filed: Dec. 9, 2003

(86) PCT No.: PCT/EP03/13920

§ 371 (c)(1),
(2), (4) Date: Feb. 14, 2006

(87) PCT Pub. No.: WO2004/056842

PCT Pub. Date: Jul. 8, 2004

(65) Prior Publication Data

US 2006/0172915 A1  Aug. 3, 2006

(30) Foreign Application Priority Data

Dec. 19, 2002 (DE) ................. 102 59 403

(51) Int. Cl.
*C11D 3/22* (2006.01)
*C11D 3/24* (2006.01)
*C11D 11/04* (2006.01)
*C07H 15/04* (2006.01)

(52) U.S. Cl. .................. 510/412; 510/470; 510/473; 510/474

(58) Field of Classification Search ................ 510/412, 510/470, 473, 474
See application file for complete search history.

(56) References Cited

U.S. PATENT DOCUMENTS

2004/0136939 A1* 7/2004 Schmid et al. ........... 424/70.13

FOREIGN PATENT DOCUMENTS

| DE | 10122255 | * 11/2002 |
| EP | WO 97/42299 | * 11/1997 |
| WO | WO 97/42299 A1 | 11/1997 |
| WO | WO 02/090369 A2 | 11/2002 |

* cited by examiner

*Primary Examiner*—Brian Mruk
(74) *Attorney, Agent, or Firm*—John F. Daniels

(57) ABSTRACT

A process for reducing the amount of halocarbons in a mixture containing water and at least one of an alkyl or alkenyl glycoside carboxylic acid. The amount of halocarbon is reduced by heating the mixture at a temperature of 50° C. to 120° C. at a pH of from 10-14. The amount of organomonochloro compounds can be reduced to a range of 5 ppm or less and the amount of organodichloro compounds can be reduced to a range of 30 ppm.

20 Claims, No Drawings

METHOD FOR PRODUCING ALKYL OLIGOGLUCOSIDE AND ALKENYL OLIGOGLUCOSIDE CARBOXYLIC ACID SALTS WITH REDUCED ORGANOCHLORIDE COMPOUNDS

RELATED APPLICATIONS

This application is filed under 35 U.S.C. § 371 claiming priority from Application PCT/EP2003/013920 filed on Dec. 9, 2003, which claims priority of German patent application DE 102 59 403.1 filed on Dec. 19, 2002, the entire contents of each application are incorporated herein by reference.

FIELD OF THE INVENTION

This invention relates generally to surface-active compounds and, more particularly, to a new process for the production of special anionic surfactants which are distinguished by a reduced content of organic chlorine compounds.

BACKGROUND OF THE INVENTION

Carboxylation products of alk(en)yl oligoglycosides are anionic surfactants which have improved foaming, viscosity and sensory properties in relation to the non-derivatized homologs. They are normally produced by reaction of the glycosides with halocarboxylic acid salts, especially sodium chloroacetate, in aqueous solution. Some or all of the hydroxyl groups available are reacted, depending upon the quantity of alkylating agent used. Since this reaction generally requires an excess of the alkylating agent, the end products always contain traces of organic chlorine compounds which can amount to as much as 2,000 ppm, based on monochloroacetate for example, or to as much as 500 ppm, based on the dichloroacetate present as an impurity in the monochloroacetate.

For cosmetic applications in particular, such quantities of organo-chlorine compounds are unacceptable because they can cause irritation of the skin or are otherwise undesirable for physiological reasons.

Accordingly, the problem addressed by the present invention was to provide an improved process for the production of alk(en)yl oligoglycoside carboxylic acid salts which would give products with a content of organochlorine compounds of less than 35 ppm and preferably less than 10 ppm.

BRIEF DESCRIPTION OF THE INVENTION

The present invention relates to a new process for the production of water-containing pastes of alkyl and/or alkenyl oligoglycoside carboxylic acid salts with a reduced content of organochlorine compounds, characterized in that the alkyl and/or alkenyl oligoglycosides are reacted in known manner with halocarboxylic acids or salts thereof and the reaction products are subjected to an alkaline aftertreatment at temperatures in the range from 50 to 120° C.

It has surprisingly been found that, by subjecting the pastes to an alkaline aftertreatment, the overall content of organic chlorine compounds can be reduced to at least below 35 ppm, and, generally, even to below 10 ppm.

DETAILED DESCRIPTION OF THE INVENTION

Alkyl and/or Alkenyl Oligoglycosides

Alkyl and alkenyl oligoglycosides, which represent one of the two starting materials for the production of the carboxylic acid salts, are known nonionic surfactants corresponding to formula (I):

$$R^1O-[G]_p \quad (I)$$

where $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 1.8 are preferred.

Halocarboxylic Acids

The carboxyl functions are introduced into the glycosides using halocarboxylic acids or salts thereof preferably corresponding to formula (II):

$$Cl(CH_2)_n COOX \quad (II)$$

in which n is a number of 1 to 5 and X is hydrogen or an alkali metal, preferably sodium or potassium. Chloroacetic acid or its sodium salt in particular is used.

Carrying out the Process

The carboxylation of the alk(en)yl oligoglycosides may be carried out in known manner, i.e. by direct reaction of the reactants in aqueous solution at elevated temperature. The alkyl and/or alkenyl oligoglycosides and the halocarboxylic acids or salts are typically used in a molar ratio of 1:0.9 to 1:5, preferably in a molar ratio of 1:1.05 to 1:3 and more particularly in a molar ratio of 1:1.2 to 1:2. The excess of halocarboxylic acids is primarily determined by the number of carboxyl functions which are to be introduced into the molecule in this way. Water-containing pastes of alkyl and/or alkenyl oligoglycoside carboxylic acid salts with a solids content of 30 to 60 and more particularly 40 to 50% by weight and contents of organic chlorine compounds of up to 2,500 ppm are obtained in this way. For degradation, the pastes are subjected to an alkaline aftertreatment, i.e. are adjusted to a pH of 10 to 14 and preferably 11 to 13 by addition of aqueous alkali metal compounds, preferably sodium or potassium hydroxide solution. It has surprisingly been found that the glycoside carboxylic acid salts are not hydrolyzed under these conditions. An aftertreatment—optionally under (autogenous) pressure—at a temperature of 60 to 110° C. and more particularly at a temperature of 70 to 90° C. has proved to be particularly advantageous. In addition, it is advisable to carry out the aftertreatment in the absence of atmospheric oxygen, i.e. under an inert gas blanket, in order to prevent discolouration of the products. The reaction time depends on the pH and the temperature together and is typically between 2 and 5 hours. It is in fact advisable to follow the progress of the aftertreatment by sampling and to terminate the reaction when the content of monochlorine compounds has fallen below 5 ppm and the content of dichlorine compounds is below 30 ppm.

EXAMPLES

Example 1

550 g of a 50% by weight water-containing paste of a $C_{12/14}$ cocoalkyl oligoglucoside carboxylate (Plantapon® LGC, Cognis Deutschland GmbH & Co. KG) with a residual content of 314 ppm monochloroacetate and 58 ppm dichloroacetate were introduced into a stirred vessel and adjusted with 13.7 g of an aqueous 50% by weight sodium hydroxide solution to a pH value of 13.5 (as measured in 10% by weight dilution). The mixture was then stirred under nitrogen for 3 h at a temperature of 90 to 95° C. The purified product was obtained as a pale yellow liquid and, after the treatment, had a monochloroacetate content of less than 1 ppm and a dichloroacetate content of less than 5 ppm.

Example 2

550 g of a 50% by weight water-containing paste of a $C_{12/14}$ cocoalkyl oligoglucoside carboxylate (Plantapon® LGC, Cognis Deutschland GmbH & Co. KG) with a residual content of 314 ppm monochloroacetate and 58 ppm dichloroacetate were introduced into a stirred vessel and adjusted with 10.4 g of an aqueous 50% by weight potassium hydroxide solution to a pH value of 13.5 (as measured in 10% by weight dilution). The mixture was then stirred under nitrogen for 2.5 h at a temperature of 90 to 95° C. The purified product was obtained as a pale yellow liquid and, after the treatment, had a monochloroacetate content of less than 1 ppm and a dichloroacetate content of less than 5 ppm.

We claim:

1. A process for the preparation of a water containing composition comprising at least one member selected from the group consisting of alkyl oligoglycoside carboxylic acid salts and alkenyl oligoglycoside carboxylic acid salts with a residual content of halocarbon compounds which comprises: heating an aqueous mixture comprising at least one pre-formed member selected from the group consisting of alkyl oligoglycoside carboxylic acid salts and alkenyl oligoglycoside carboxylic acid salts, water and residual halocarbon compounds at a pH of from 10 to 14 and a temperature of from 50° to 120° C., whereby a mixture with a reduced content of residual halocarbon compounds is formed.

2. The process of claim 1 which further comprises:
   (1) reacting an aqueous mixture comprising at least one member selected from the group consisting of alkyl oligoglycosides and alkenyl oligoglycosides with at least one member selected from the group consisting of halocarboxylic acids and halocarboxylic acid salts to form an aqueous reaction mixture containing alkyl oligoglycoside carboxylic acid salts, alkenyl oligoglycoside carboxylic acid salts and residual halocarbon compounds; and
   (2) heating the aqueous reaction mixture at a pH of from 10 to 14 to form a heated reaction mixture with a reduced content of residual halocarbon compounds.

3. The process as claimed in claim 2, wherein the alkyl and/or alkenyl oligoglycoside comprises a composition of the formula:

$$R^1O\text{---}[G]_p \quad (I)$$

where $R^1$ is an alkyl and/or alkenyl group containing 4 to 22 carbon atoms, G is a sugar unit containing 5 or 6 carbon atoms and p is a number of 1 to 10.

4. The process as claimed in claim 3, wherein the oligoglycoside comprises an alkyl glucoside of the formula (I), wherein $R^1$ is a $C_{12-18}$ alkyl group, G is a glucose residue and p is a number of 1 to 1.8.

5. The process as claimed in claim 2, wherein the halocarboxylic acid or salt thereof comprises a compound of the formula:

$$Cl(CH_2)_n COOX \quad (II)$$

wherein n is a number of 1 to 5 and X is hydrogen or an alkali metal.

6. The process as claimed in claim 2, wherein the halocarboxylic acid or halocarboxylic acid salt comprises chloroacetic acid or its sodium salt.

7. The process as claimed in claim 2, wherein the alkyl and/or alkenyl oligoglycosides and the halocarboxylic acid or its salt are used in a molar ratio of 1:0.9 to 1:5.

8. The process as claimed in claim 1, wherein the aqueous mixture comprises at least one member selected from the group consisting of alkyl oligoglycoside carboxylic acid salts and alkenyl oligoglycoside carboxylic salts in a concentration of 30 to 60% by weight.

9. The process as claimed in claim 1, wherein the pH of the aqueous mixture is adjusted to a range of 10 to 14 by addition of aqueous alkali metal compounds.

10. The process as claimed in claim 1, wherein the aqueous mixture is heated at a temperature of 70 to 90° C.

11. The process as claimed in claim 1, wherein the aqueous mixture contains residual organochlorine compounds and is heated until a content of residual organomonochlorine compounds is below 5 ppm and a content of residual organodichlorine compounds is below 30 ppm.

12. The process of claim 2, wherein the aqueous reaction mixture of step (1) comprises at least one member selected from the group consisting of alkyl oligoglycoside carboxylic acid salts and alkenyl oligoglycoside carboxylic salts in a concentration of 30 to 60% by weight.

13. The process of claim 2, wherein the pH of the aqueous reaction mixture of step (1) is adjusted to a range of 10 to 14 by addition of aqueous alkali metal compounds.

14. The process of claim 2, wherein in step (2) the aqueous reaction mixture is heated at a temperature of 70 to 90° C.

15. The process of claim 2, wherein the aqueous reaction mixture of step (1) contains residual organo chlorine compounds and is heated until a content of residual organomonochlorine compounds is below 5 ppm and a content of residual organodichlorine compounds is below 30 ppm.

16. The process of claim 3, wherein the aqueous mixture comprises at least one member selected from the group consisting of alkyl oligoglycoside carboxylic acid salts and alkenyl oligoglycoside carboxylic salts in a concentration of 30 to 60% by weight.

17. The process of claim 3, wherein the pH of the aqueous mixture is adjusted to a range of 10 to 14 by addition of aqueous alkali metal compounds.

18. The process of claim 3, wherein the aqueous mixture is heated at a temperature of 70 to 90° C.

19. The process of claim 3, wherein the aqueous mixture contains residual organo chlorine compounds and is heated until a content of residual organomonochlorine compounds is below 5 ppm and a content of residual organodichlorine compounds is below 30 ppm.

20. The process of claim 5, wherein the aqueous mixture comprises at least one member selected from the group consisting of alkyl oligoglycoside carboxylic acid salts and alkenyl oligoglycoside carboxylic salts in a concentration of 30 to 60% by weight.

* * * * *